United States Patent
Li et al.

(10) Patent No.: US 10,387,419 B2
(45) Date of Patent: Aug. 20, 2019

(54) METHOD AND SYSTEM FOR MANAGING DATABASES HAVING RECORDS WITH MISSING VALUES

(71) Applicant: SAP SE, Walldorf (DE)

(72) Inventors: Wen-Syan Li, Fremont, CA (US); Yu Cheng, Shanghai (CN)

(73) Assignee: SAP SE, Walldorf (DE)

( * ) Notice: Subject to any disclaimer, the term of this patent is extended or adjusted under 35 U.S.C. 154(b) by 663 days.

(21) Appl. No.: 14/045,656

(22) Filed: Oct. 3, 2013

(65) Prior Publication Data

US 2015/0088907 A1 Mar. 26, 2015

(30) Foreign Application Priority Data

Sep. 26, 2013 (CN) .......................... 2013 1 0445615

(51) Int. Cl.
*G06F 16/2455* (2019.01)
*G16H 10/60* (2018.01)

(52) U.S. Cl.
CPC ....... *G06F 16/24554* (2019.01); *G16H 10/60* (2018.01)

(58) Field of Classification Search
CPC ......... H01L 2924/0002; H01L 2924/00; C08F 259/04; G06K 9/46; G06T 7/0012
USPC ....................................................... 707/737
See application file for complete search history.

(56) References Cited

U.S. PATENT DOCUMENTS

| | | | |
|---|---|---|---|
| 5,537,590 A * | 7/1996 | Amado | |
| 6,047,287 A * | 4/2000 | Caruana | G06F 17/17 |
| 8,065,257 B2 * | 11/2011 | Kuecuekyan | 706/46 |
| 8,443,013 B1 * | 5/2013 | Lin | G06Q 10/04 707/810 |
| 8,521,564 B1 * | 8/2013 | Ciechanowski | 705/3 |
| 2007/0214133 A1 * | 9/2007 | Liberty | G06F 17/3064 |
| 2009/0299767 A1 * | 12/2009 | Michon et al. | 705/3 |
| 2010/0082362 A1 * | 4/2010 | Salsbury et al. | 705/1.1 |
| 2010/0088336 A1 * | 4/2010 | Johnston et al. | 707/770 |
| 2011/0066577 A1 * | 3/2011 | Van Gael | G06N 99/005 706/12 |
| 2011/0179051 A1 * | 7/2011 | Bruckner | G06Q 10/00 707/758 |
| 2012/0123981 A1 * | 5/2012 | Graves et al. | 706/13 |
| 2012/0158678 A1 * | 6/2012 | McGraw et al. | 707/694 |
| 2013/0054552 A1 * | 2/2013 | Hawkins et al. | 707/706 |
| 2013/0185294 A1 * | 7/2013 | Kami | 707/732 |
| 2013/0204886 A1 * | 8/2013 | Faith et al. | 707/756 |
| 2013/0226613 A1 * | 8/2013 | Srinivasan | G06Q 50/24 705/3 |

* cited by examiner

*Primary Examiner* — Hosain T Alam
*Assistant Examiner* — Nicholas E Allen
(74) *Attorney, Agent, or Firm* — Klarquist Sparkman, LLP (57) ABSTRACT

The method includes selecting a target record from a dataset, the target record including a missing value, partitioning records of the dataset into at least two groups including co-related data, the partitioned records including records having a value for a same field as the missing value in the target record, predicting the missing value based on a relationship between fields in each of the at least two groups associated with the partitioned records, and setting the missing value of the target record to the predicted value.

17 Claims, 9 Drawing Sheets

| ID (505) | C_1 (510) | C_2 (515) | C_3 (520) | ... | C_30 (530) | C_31 (535) | C_32 (540) |
|---|---|---|---|---|---|---|---|
| 1 | 68 | 164 | 0.55 | ... | 0.75 | 0.33 | 0.8 |
| 2 | 70 | 177 | 0.62 | ... | 0.28 | 0.29 | 0.9 |
| 3 | 80 | 128 | 0.81 | ... | 0.45 | 0.5 | 0.6 |
| 4 | 64 | 145 | 0.28 | ... | NaN | 1.00 | 0.3 |
| 5 | 72 | 180 | 0.44 | ... | 1.00 | 0.4 | 0.7 |
| : | : | : | : | : | : | : | : |
| 20 | 65 | 122 | NaN | ... | 0.8 | 0.55 | 0.7 |

Missing Data (545) — row 4, C_30 column (NaN)

First Type Data | Second Type Data

Missing Data (550) — row 20, C_3 column (NaN)

METHOD AND SYSTEM FOR MANAGING DATABASES HAVING RECORDS WITH MISSING VALUES

CROSS REFERENCE TO RELATED APPLICATIONS

This application claims priority under 35 U.S.C. § 119 to Chinese Patent Application 201310445615.0, filed Sep. 26, 2013, titled "A METHOD AND SYSTEM FOR MANAGING DATABASES HAVING RECORDS WITH MISSING VALUES," which is incorporated herein by reference in its entirety.

FIELD

Embodiments relate to managing databases having records with missing values. More specifically, embodiments relate to imputing a value for the missing values in the records.

BACKGROUND

In any dataset (e.g., data table or query result) of a database (or other data store, for example an XML file), there is the possibility of having entries of a record (or recordset) with missing values. For example, collected data may be missing values because the value is unknown at the time the data is collected. Missing data affects the quality of the data in, for example, in analysis or research based on the data.

As an example, personal health record (PHR) databases play an important role in promotion of medical and disaster research, as well as providing analytic service for personal health care. For example, a PHR can provide personal health analysis according to historical data from the database. The historical data may support counselors and instructors in various types of health promotion facilities. Moreover, health maintenance cycle brought by wellness tour can be scheduled and reminded by PHR analysis. In addition, the data can be used to create a prediction model to recommend the best wellness program or a healthy daily menu. Generally, PHR data can be collected based on three main approaches: daily health records from personal health meters, custom records from wellness centers and statistical database from universities and research centers. However, missing values occur in the PHR databases there may be some difficulty in collecting complete data for all the people.

In conventional missing value imputation methods, a selected record with a missing value can be expressed as a linear combination of all the other similar records. In other words, these algorithms exploit local similarity structure in the dataset for missing value imputation. Typically, a subset of records that exhibits high correlation with the record containing the missing values is used to impute the missing value. Most methods also assume that the features of all the records are considered independent with each other, most of which have been applied in microarray data analysis.

However, in some databases (or datasets), some data features may be linearly co-related, and the data can be categorized based on the relationship. For example, PHR data may be categorized into two groups by their features. One group may be measured data, such as height, weight, blood test results; the other group may be generated and quantified from questionnaires, such as tiredness, appetite. Accordingly, the types of features may affect the linear combination differently. Conventional missing value imputation methods do not consider co-related data when imputing missing values in a database. Accordingly, there is a need to methods and systems to utilize co-related data when imputing missing values in a database.

SUMMARY

One embodiment includes a method. The method includes selecting a target record from a dataset, the target record including a missing value, partitioning records of the dataset into at least two groups including co-related data, the partitioned records including records having a value for a same field as the missing value in the target record, predicting the missing value based on a relationship between fields in each of the at least two groups associated with the partitioned records, and setting the missing value of the target record to the predicted value.

Another embodiment includes a non-transitory computer-readable storage medium having stored thereon computer executable program code which, when executed on a computer system, causes the computer system to perform steps. The steps include selecting a target record from a dataset, the target record including a missing value, partitioning records of the dataset into at least two groups including co-related data, the partitioned records including records having a value for a same field as the missing value in the target record, predicting the missing value based on a relationship between fields in each of the at least two groups associated with the partitioned records, and setting the missing value of the target record to the predicted value.

Still another embodiment includes an apparatus. The apparatus includes a value prediction module configured to select a target record from a dataset, the target record including a missing value, and configured to set the missing value of the target record to a predicted value. The apparatus includes a model generation module configured to partition records of the dataset into at least two groups including co-related data, the partitioned records including records having a value for a same field as the missing value in the target record, and configured to predict the missing value based on a relationship between fields in each of the at least two groups associated with the partitioned records.

BRIEF DESCRIPTION OF THE DRAWINGS

Example embodiments will become more fully understood from the detailed description given herein below and the accompanying drawings, wherein like elements are represented by like reference numerals, which are given by way of illustration only and thus are not limiting of the example embodiments and wherein:

FIG. 5 illustrates a dataset according to at least one example embodiment.

It should be noted that these Figures are intended to illustrate the general characteristics of methods and/or structure utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the positioning of structural elements may be reduced or exaggerated for clarity. The use of similar or identical reference numbers in the various drawings is intended to indicate the presence of a similar or identical element or feature.

DETAILED DESCRIPTION OF THE EMBODIMENTS

While example embodiments may include various modifications and alternative forms, embodiments thereof are shown by way of example in the drawings and will herein be described in detail. It should be understood, however, that there is no intent to limit example embodiments to the particular forms disclosed, but on the contrary, example embodiments are to cover all modifications, equivalents, and alternatives falling within the scope of the claims. Like numbers refer to like elements throughout the description of the figures.

Example embodiments describe a bi-local linear model where two local linear sub-models are constructed and interpolated using two types of co-related data. For example, the first type of co-related data may be based on quantitative (e.g., measured) data and the second type of co-related data may be based on qualitative (or subjective) data. In an example implementation of a PHR database, the first type (or quantitative) of co-related data may be vital data and second type (or qualitative) of co-related data may be questionnaire data, respectively. Accordingly, in contrast to conventional imputation methods, not only local similarity information is utilized, but also correlation between data features is considered.

Figure 1:
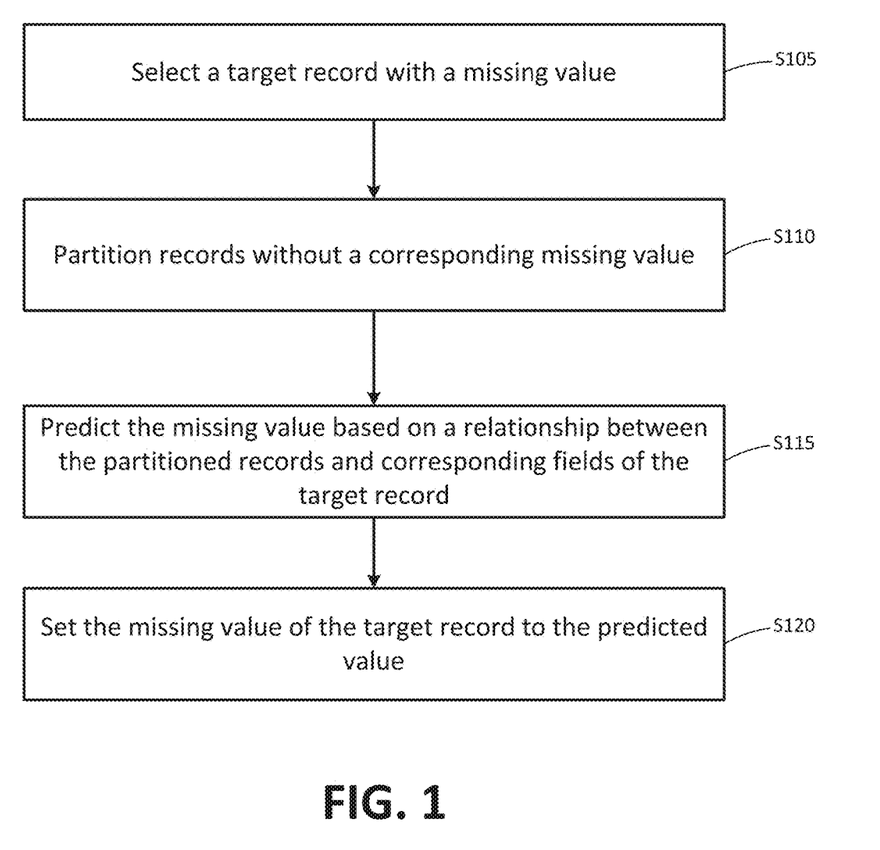
FIG. 1 illustrates a method according to at least one example embodiment.
Figure 2:
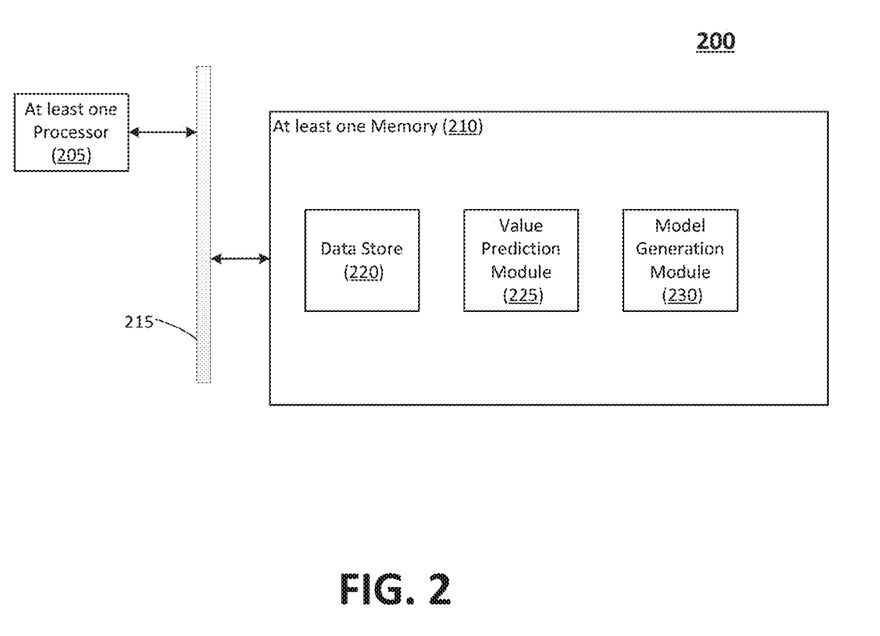
FIG. 2 illustrates a block diagram of a system according to at least one example embodiment.

FIG. 1 illustrates a method according to at least one example embodiment. The method steps described with regard to FIG. 1 may be executed as software code stored in a memory (e.g., at least one memory 210 described below) associated with a system (e.g., as shown in FIG. 2) and executed by at least one processor (e.g., at least one processor 205 described below) associated with the system. However, alternative embodiments are contemplated such as a system embodied as a special purpose processor.

For example, the method steps may be performed by an application-specific integrated circuit, or ASIC. For example, the ASIC may be configured as one or more of the blocks, or elements of the blocks, (e.g., the value prediction module 225 described below) and/or the system 200. Although the steps described below are described as being executed by a processor, the steps are not necessarily executed by a same processor. In other words, at least one processor may execute the steps described below with regard to FIG. 1.

As shown in FIG. 1, in step S105 a processor (e.g., at least one processor 205) selects a target record with a missing value. For example, the processor may filter a dataset to include records with missing values. In some example implementations, the processor may select a target record as a record with the fewest number of missing values. In this case, the processor may filter the dataset to include one (1) missing value. If the resultant filtered dataset includes zero (0) records, the processor may filter the dataset to include two (2) missing value. This process may continue until the resultant filtered dataset includes at least one (1) record. Then, the processor may randomly select a record from the resultant filtered dataset as the target record.

In step S110 the processor partitions records without a corresponding missing value. For example, the records without a corresponding missing value may be all (or a subset of) the records in the dataset not including the target record. Accordingly, the processor may filter the dataset to exclude the target record. Further, the processor may partition the resultant filtered dataset based on some co-related data characteristics. For example, the processor may partition the resultant filtered dataset in to two types of co-related data. For example, the first type of co-related data may be based on quantitative (e.g., measured) data and the second type of co-related data may be based on qualitative (or subjective) data. However, example embodiments are not limited to groups including quantitative and qualitative data. Accordingly, the processor partitions records of the dataset into at least two groups including co-related data, the partitioned records including records having a value for a same field as the missing value in the target record.

In step S115 the processor predicts the missing value based on a relationship between the partitioned records and corresponding fields of the target record. The processor may predict the missing value based on a relationship between fields in each of the at least two groups associated with the partitioned records. For example, the processor may generate a bi-local linear model (described in more detail below) where two local linear sub-models are generated and interpolated using the two types of co-related data. The processor may then use the bi-local linear model to predict the missing value. Then, in step S120 the processor sets the missing value of the target record to the predicted value. For example, the processor may write the predicted value in the corresponding field of the target record.

FIG. 2 illustrates a block diagram of a system according to at least one example embodiment. As shown in FIG. 2, the system (or apparatus) 200 includes at least one processor 205 and at least one memory 210. The at least one processor 205 and the at least one memory 210 are communicatively coupled via bus 215. The system 200 may be, for example, an element of a computing device (e.g., a cloud computing device, a server or a personal computer).

In the example of FIG. 2, the system 200 may be at least one computing device and should be understood to represent virtually any computing device configured to perform the methods described herein. As such, the system 200 may be understood to include various standard components which may be utilized to implement the techniques described herein, or different or future versions thereof. By way of example, the system 200 is illustrated as including the at least one processor 205, as well as the at least one memory 210 (e.g., a non-transitory computer readable storage medium) respectively.

Thus, as may be appreciated, the at least one processor 205 may be utilized to execute instructions stored on the at least one memory 210, so as to thereby implement the various features and functions described herein, or additional or alternative features and functions. Of course, the at least one processor 205 and the at least one memory 210 may be utilized for various other purposes. In particular, it may be appreciated that the at least one memory 210 may be understood to represent an example of various types of memory and related hardware and software which might be used to implement any one of the modules described herein. Systems and/or methods described below may include data and/or storage elements. The data and/or storage elements (e.g., data base tables) may be stored in, for example, the at least one memory 210.

As shown in FIG. 2, the at least one memory 210 includes a data store 220 and a value prediction module 225 and a model generation module 230. The data store 220 may be a database (including data tables or datasets) or some other data structure (e.g., an XML file). The value prediction module 225 may be configured to use the model (e.g., bi-local linear model) to predict a missing value. The value prediction module 225 may also be configured to set a field in a record to the predicted value.

The model generation module 230 may be configured to partition a dataset (e.g., excluding a record including a missing value to be predicted) in to two types of co-related data. For example, the first type of co-related data may be based on quantitative (e.g., measured) data and the second type of co-related data may be based on qualitative (or subjective) data. The model generation module 230 may be configured to generate a first linear function based on the first type of co-related data. The model generation module 230 may be configured to generate a second linear function based on the second type of co-related data. Each of the first linear function and the second linear function may be weighted (or scaled) and combined to generate a bi-local linear model for predicting a missing value. Although, two types of co-related data resulting in the generation of a bi-local linear model are discussed, example embodiments are not limited thereto. For example, any number N of co-related data partitions may be generating resulting in the generation of a N-local linear model.

Figure 3:
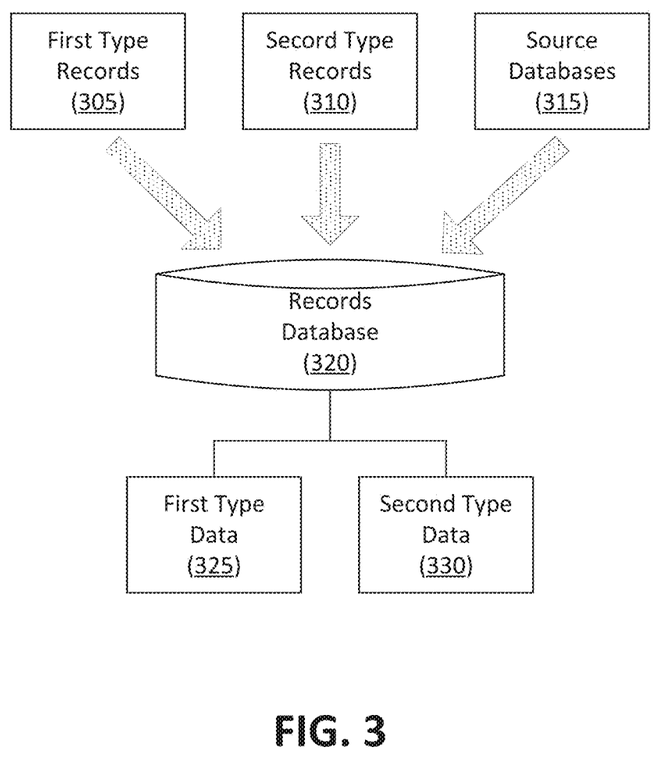
FIG. 3 illustrates a block diagram of a data store according to at least one example embodiment.

FIG. 3 illustrates a block diagram of a data store according to at least one example embodiment. As shown in FIG. 3, the data store includes a records database 320 which receives records from several data sources including, for example, a first type records 305, a second type records 310 and a source databases 315. The records database 320 may be partitioned into two types of data including, for example, a first type data 325 and a second type data 330. The two types of data may be co-related data. For example, the first type of co-related data (e.g., first type data 325) may be based on quantitative (e.g., measured) data and the second type of co-related data (e.g., second type data 330) may be based on qualitative (or subjective) data. For example, PHR data may be categorized into two groups by their features. One group (e.g., first type data 325) may be measured data, such as height, weight, blood test results; the other group (e.g., second type data 330) may be generated and quantified from questionnaires, such as tiredness, appetite.

Figure 4:
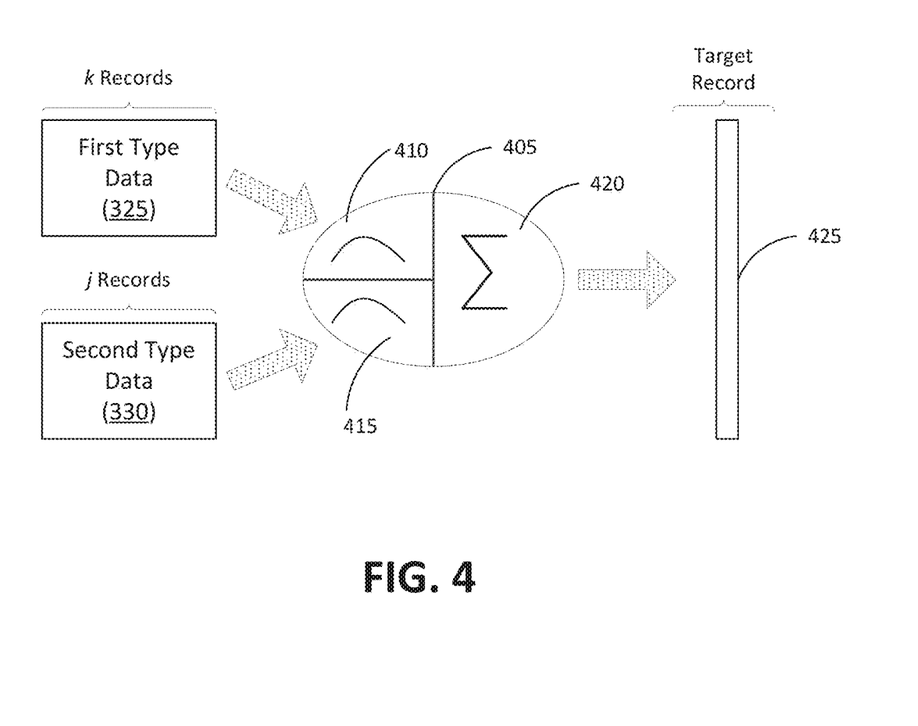
FIG. 4 illustrates a block diagram for generating a model according to at least one example embodiment.

FIG. 4 illustrates a block diagram for generating a model according to at least one example embodiment. As shown in FIG. 4, k records of the first type data 325 and j records (k may or may not equal j) of the second type data 330 are input into block 405 where a first linear function 410 is generated based on the k records of the first type data 325 and a second linear function 415 is generated based on the j records of the second type data 330. Each of the first linear function 410 and the second linear function 415 may be weighted (or scaled) and combined to generate a bi-local linear model 420 for predicting a missing value. The bi-local linear model 420 is used to predict a missing value which is then inserted into a target record 425. Although, two types of co-related data resulting in the generation of a bi-local linear model are discussed, example embodiments are not limited thereto. For example, any number N of co-related data partitions may be generating resulting in the generation of a N-local linear model.

FIG. 5 illustrates a dataset according to at least one example embodiment. The dataset includes a plurality of columns (fields or features) 505-540 and a plurality of rows (or recordsets). The dataset includes missing data 545, 550 denoted as NaN. The dataset also shows columns (fields or features) 505-525 as first type data (e.g., first type data 325) and shows columns (fields or features) 530-540 as second type data (e.g., second type data 330).

In an example implementation, a PHR database D contains N records and n features of wellness indices (columns), such as weight, basal-metabolism. In FIG. 5, an example of PHR data is shown, where NaN denotes a missing value in the database, and the data is categorized into vital data (first type data) and questionnaire data (second type data) in terms of data properties. Accordingly, in this example implementation, with respect to any missing data $y_{i,j}$ (i=1, 2, . . . , n, j=1, 2, . . . , N), the imputation can be regarded as a prediction problem by $y_{i,j}=f(x_{i,j})$ where $x_{i,j}$ represents measured data in the PHR database without the missing value.

Figure 6:
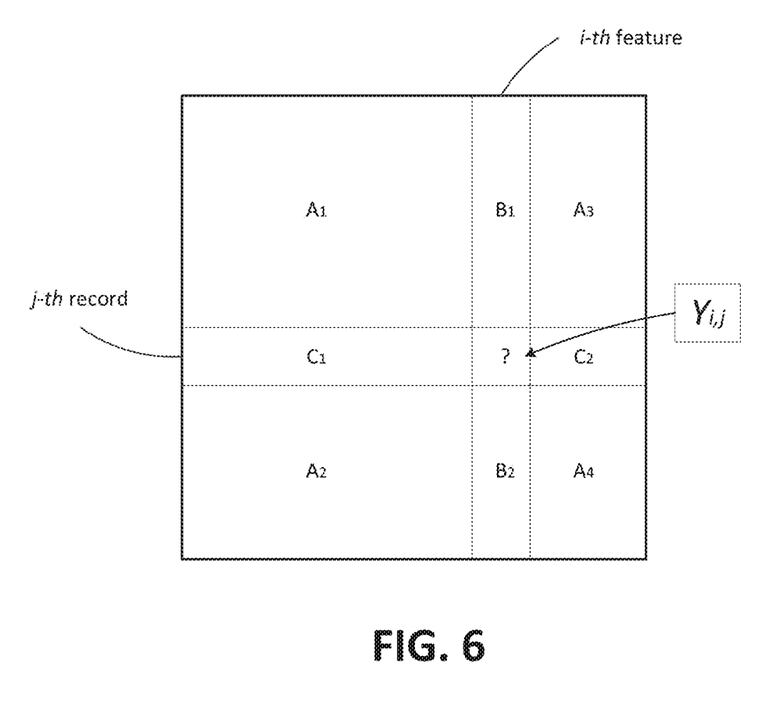
FIG. 6 illustrates another dataset according to at least one example embodiment.

FIG. 6 illustrates another dataset (or a subset of the dataset shown in FIG. 5) according to at least one example embodiment. In FIG. 6, according to some example implementations, in order to estimate the missing value $y_{i,j}$, a model is estimated as estimate $y_{i,j}$ by using $$A = \begin{bmatrix} A_1 & A_2 \\ A_3 & A_4 \end{bmatrix}, B = [B_1 B_2]^T \text{ and } C = [C_1^T C_2^T]^T.$$

Because each feature is considered equally ordered, $[A_1 A_2]^T$ may represent the first type of co-related data (e.g., first type data 325 or vital data), and $[A_3 A_4]^T$ may represent the second type of co-related data (e.g., second type data 330 or the questionaries' data).

Figure 7:
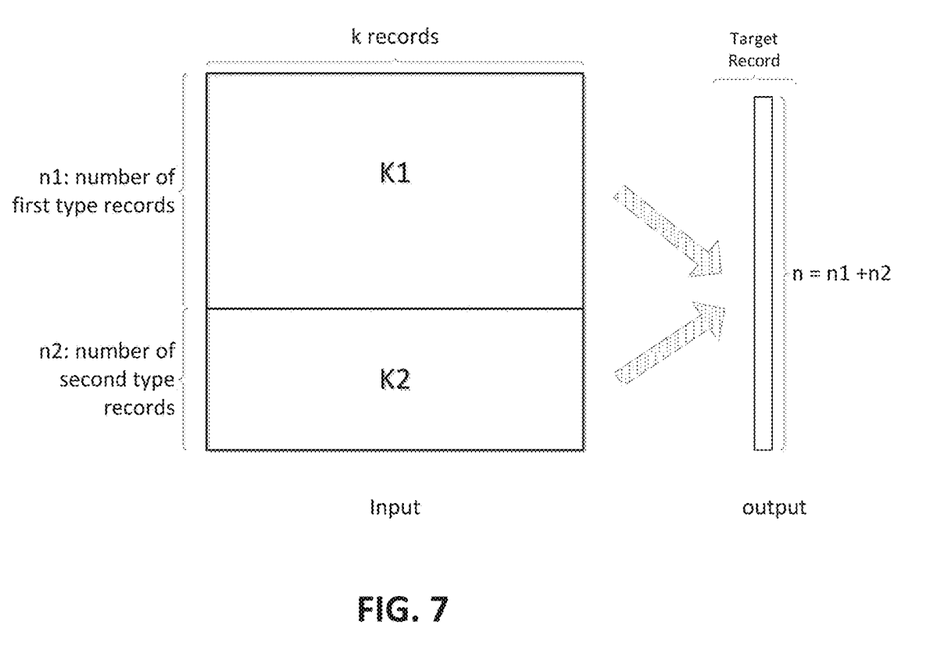
FIG. 7 illustrates a block diagram for input/output used in generating the model according to at least one example embodiment.

FIG. 7 illustrates a block diagram for input/output used in generating the model according to at least one example embodiment. As shown in FIG. 7, k records of a number (of columns, fields or features) n1 of the first type of data (e.g., first type data 325) and k records of a number (of columns, fields or features) n2 (n1 may or may not equal n2) of the second type data (e.g., second type data 330) are inputs used to generate an output (to a target record) n=n+1.

In FIG. 7 k may be the k-nearest neighbor (KNN) records of the target record. In other words, local similarity information may utilized in imputing the missing value by filtering the dataset to include the KNN records or records having similarities within a threshold value. For example, referring to FIG. 5, if missing data 550 is being imputed feature (or column) 510 may be limited to +/−5 of the value in the target record (e.g., the record with an ID 505=20). The result of the filter may be that records including a value range of 60-70 (e.g., the records with an ID 505=1, 2, and 4) may be utilized as the KNN.

Figure 8:
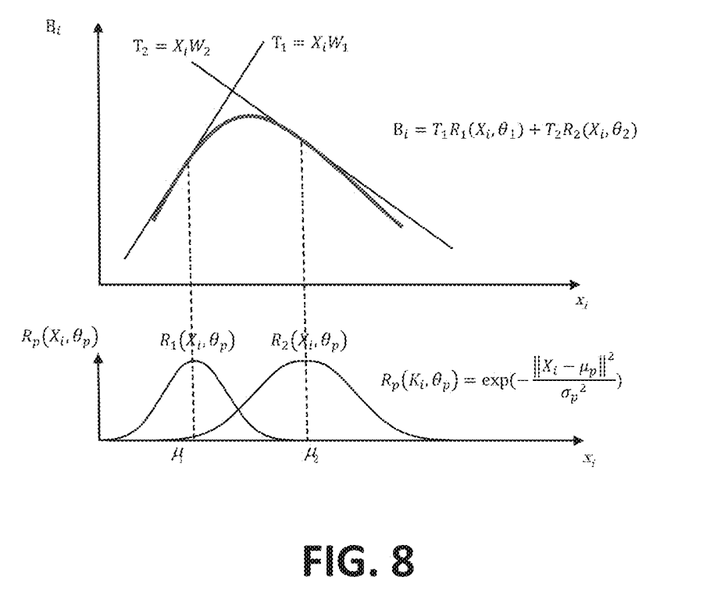
FIG. 8 illustrates a graph of a one-dimensional bi-local linear model according to at least one example embodiment.

FIG. 8 illustrates a graph of a one-dimensional bi-local linear model according to at least one example embodiment. The graph may represent a model according to example embodiments used to represent some of the dynamics between missing data and non-missing data. The model may give different weights to the first type of co-related data (e.g., first type data 325 or vital data), and the second type of co-related data (e.g., second type data 330 or the questionnaires' data). The model may be expressed as:

$$B_i = \sum_{p=1}^{2} X_i W_p R_p(X_i, \theta_p) \quad (1)$$

where
B=[$B_1 B_2$]$^T$ are the target vector;
$B_i$ denotes the i-th element (feature);
$X_i$ is the i-th feature vector of all the k-nearest neighbor records;
$W_p$ is parameter matrix of the model by $W_p = [w_{1p}, w_{2p}, \ldots, w_{np}]^T$;
$R_p(X_i, \theta_p)$ is a radial basis function with input vector $X_i$ and parameter vector θ.

Specifically $R_p(X_i, \theta_p)$ is represented as:

$$R_p(X_i, \theta_p) = \exp\left(-\frac{\|X_i - \mu_p\|^2}{\sigma_p^2}\right) \quad (2)$$

From Eq. (1), the model may be implemented as a bi-local linear model, where $T_1 = X_i W_1$ and $T_2 = X_i W_2$ are two linear sub-models; $R_p(X_i, \theta_p)$, p=1, 2 is a weighting function to interpolate the two linear sub-models. $\theta_p = [\mu_p, \sigma_p]$ is a parameter vector for the radial basis function, which introduces local property for each linear sub-model. This idea can be better illustrated by a one-dimension case in FIG. 8, where a nonlinear function is approximated by two linear sub-models. However, the work area of each sub-model may be defined in a smooth and flexible way. Therefore, radial basis functions may applied in the two sub-regions, which provide local linear work area and give different weights to both two local linear sub-models.

We regard vital features and questionnaire features separately to obtain the two local linear sub-regions. Therefore, both the two kinds of data will contribute to the target record with different weights on each feature.

To identify parameters of the proposed model, two steps may be implemented.
1. Estimation of $\theta_p$: this parameter vector contains $\mu_p$, $\sigma_p$ in the radial basis function. $\mu_p$ is center parameter for the location of function, and it can be determined as center of each local linear region. Specifically, $\mu_p$ can be determined as centers of vital dataset and questionnaire dataset in the multi-dimensional space. $\sigma_p$ is scale parameter for the shape of function, thereby can be determined as variances of each dataset.
2. Estimation of $W_p$: when parameter vector $\theta_p$ is determined and fixed, the model as Eq. (1) shown can be transferred in a linear-in-parameter model:

$$B_i = \Phi(X_i)^T \Theta \quad (3)$$

where $$\Phi(X_i) = [X_i R_1(X_i), X_i R_2(X_i)] \quad (4)$$

$$\Theta = [w_{11}, w_{21}, \ldots, w_{n1}, w_{11}, w_{22}, \ldots, w_{n2}]^T \quad (5)$$

Accordingly, parameter Θ can be estimated as a least square algorithm. Finally, the missing value y may be estimated by using the identified model:

$$y = \Phi(C)^T \Theta \quad (6)$$

where
C denotes the target record including the other non-missing data.

The imputation problem defined above falls into the category of prediction. As a result, the main process of imputation can be roughly divided into two steps:
1. Determining or generating a model f according to the matrix A and B follows by B=f (A), which models the dynamics between records without missing values (all the records except i-th one) and the one with missing value (i-th record).
2. Predicting the missing value by estimated model f as $y_{i,j} = f(C)$.

Further, the first type of co-related data (e.g., first type data 325 or vital data), and the second type of co-related data (e.g., second type data 330 or the questionnaires' data) often take different characteristics in the dataset. Accordingly, in some implementations the first type of co-related data (e.g., first type data 325 or vital data), and the second type of co-related data (e.g., second type data 330 or the questionnaires' data) may be given different weights (or be scaled) in the imputation process.

In the pre-processing step, a target record with least number of missing values is selected. Except for the missing data to be estimated, all the other missing data are imputed roughly in a mean imputation approach, which are simply estimated as mean value of all the other records' feature value for the certain feature.

In the modeling step, KNN records of the target record are selected firstly, which is denoted by K (can be divided into $K_1$ and $K_2$ with respect to the first type of co-related data (e.g., first type data 325 or vital data), and the second type of co-related data (e.g., second type data 330 or the questionnaires' data), respectively). In order to keep the proposed method from over-fitting, the KNN may be used to select similar records to utilize in missing data estimation. Further, the dataset for model determination/generation purposes may be formatted as shown in FIG. 7. The target record with missing value may modeled by using KNN, while the first type of co-related data (e.g., first type data 325 or vital data), and the second type of co-related data (e.g., second type data 330 or the questionnaires' data) may separately contribute to the output. Each of these steps is further detailed in FIG. 9.

Figure 9:
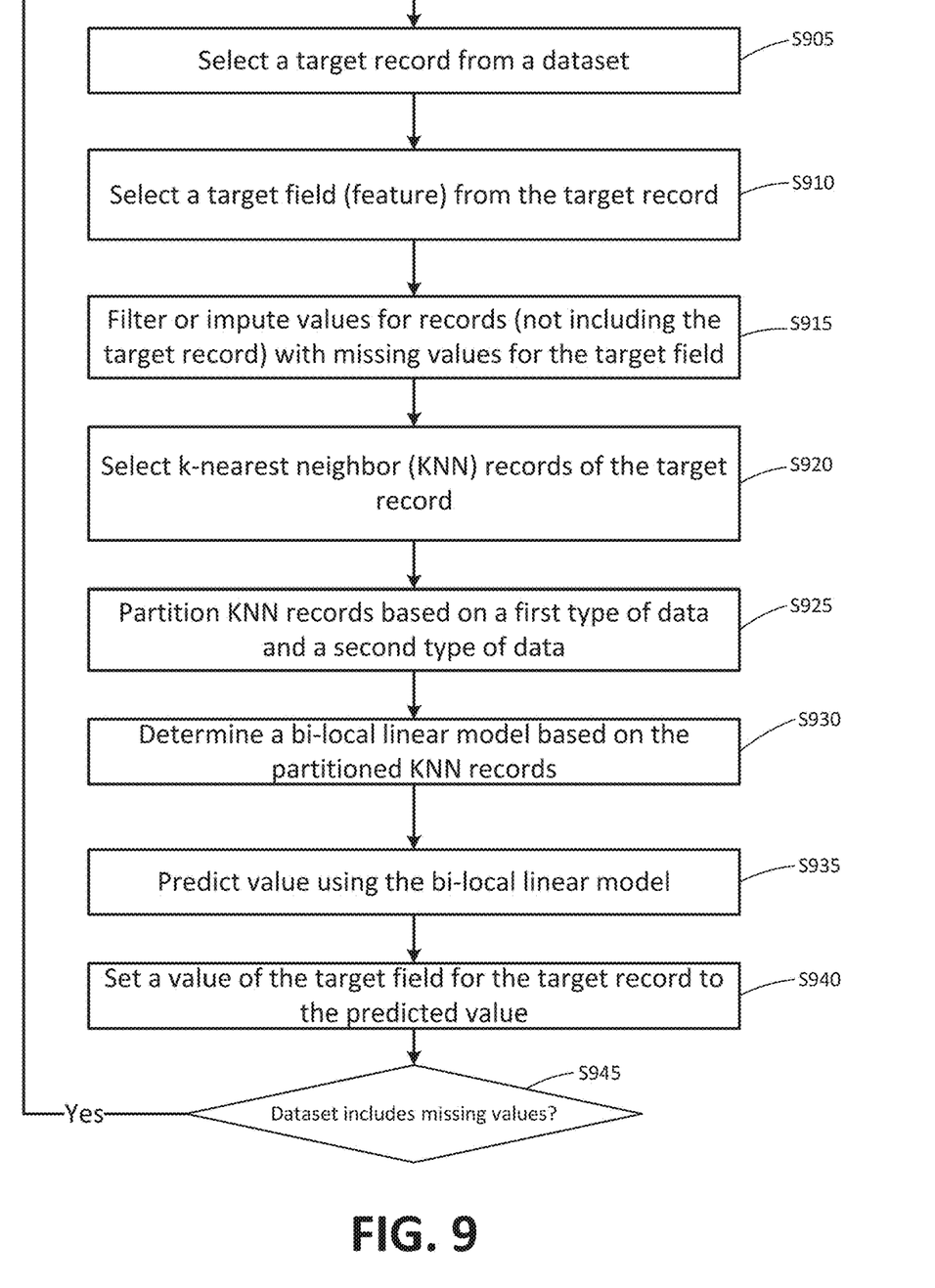
FIG. 9 illustrates another method according to at least one example embodiment.

FIG. 9 illustrates another method according to at least one example embodiment. The method steps described with regard to FIG. 9 may be executed as software code stored in a memory (e.g., at least one memory 210) associated with a system (e.g., as shown in FIG. 2) and executed by at least one processor (e.g., at least one processor 205) associated with the system. However, alternative embodiments are contemplated such as a system embodied as a special purpose processor.

For example, the method steps may be performed by an application-specific integrated circuit, or ASIC. For example, the ASIC may be configured as one or more of the blocks, or elements of the blocks, (e.g., the value prediction module 225) and/or the system 200. Although the steps described below are described as being executed by a processor, the steps are not necessarily executed by a same processor. In other words, at least one processor may execute the steps described below with regard to FIG. 9.

As shown in FIG. 9, in step S905 a processor (e.g., at least one processor 205) selects a target record from a dataset. For example, the processor may filter a dataset to include records with missing values. In some example implementations, the processor may select a target record as a record with missing values and/or a record with the fewest number of missing values. In this case, the processor may filter the dataset to include one (1) missing value. If the resultant filtered dataset includes zero (0) records, the processor may filter the dataset to include two (2) missing value. This process may continue until the resultant filtered dataset includes at least one (1) record. Then, the processor may randomly select a record from the resultant filtered dataset as the target record.

In step S910 the processor selects a target field (feature) from the target record. For example, the processor may select a field (feature or column) including a missing value (e.g., the field including missing data 550) the target field.

In step S915 the processor filters or imputes values for records (not including the target record) with missing values for the target field. For example, in some example implementations the dataset may include a large number of records. Accordingly, a number of records (not including the selected target record) missing values for the selected target field may be below a threshold value. Therefore, the processor may filter the dataset to exclude from the dataset those records missing values for at least one target field, the at least one target field including the missing value. For example, the processor may filter the dataset to exclude (or temporarily remove) from the dataset those records missing values for the selected target field. Alternatively, or in addition to, the processor may determine (e.g., impute) a mean or average value for the selected target field and insert the mean or average value as a temporary value for each record missing a corresponding value for the selected target field. The aforementioned threshold value may be based on having a statistically significant or sufficient number of records (e.g., k-records) to model the resultant dataset.

In step S920 the processor selects k-nearest neighbor (KNN) records of the target record. For example, the k-nearest neighbor (KNN) records of the target record may infer local similarity within each of the first type of co-related data (e.g., first type data 325 or vital data), and the second type of co-related data (e.g., second type data 330 or the questionnaires' data), respectively (whether or not the dataset is filtered based on the first type of co-related data and/or the second type of co-related data at this point in the method). In other words, local similarity information may utilized in imputing the missing value by filtering the dataset to include the KNN records or records having similarities within a threshold value. For example, referring to FIG. 5, if missing data 550 is being imputed feature (or column) 510 may be limited to +/−5 of the value in the target record (e.g., the record with an ID 505=20). The result of the filter may be that records including a value range of 60-70 (e.g., the records with an ID 505=1, 2, and 4) may be utilized as the KNN.

In step S925 the processor partitions the KNN records based on a first type of data and a second type of data. For example, the processor may partition the KNN records based on some co-related data characteristics. For example, the processor may partition the KNN records into two types of co-related data. For example, the first type of co-related data may be based on quantitative (e.g., measured) data and the second type of co-related data may be based on qualitative (or subjective) data. However, example embodiments are not limited thereto. For example, the processor may generate two datasets as KNN records of first type data 325 and KNN records of second type data 330 (referring to FIGS. 3 and 4). For example, referring to FIG. 5, a first dataset may include columns (fields or features) 505-525 as first type data (e.g., first type data 325) and second dataset may include columns (fields or features) 530-540 as second type data (e.g., second type data 330).

In step S930 the processor determines a bi-local linear model based on the partitioned KNN records. For example, as discussed above, the processor may generate a first linear function (e.g., first linear function 410) based on the first type of co-related data and a second linear function (e.g., second linear function 415) based on the second type of co-related data. The two linear functions may be represented as sub-models $T_1=X_iW_1$ and $T_2=X_iW_2$ discussed above with regard to eqn. 1. Each of the first linear function and the second linear function may be weighted (or scaled) and combined to generate a bi-local linear local model for predicting a missing value as discussed above with regard to eqns. 1-6.

In step S935 the processor predicts a value using the bi-local linear model. For example, as discussed in more detail above, the processor may use the bi-local linear model to predict the missing value. For example, the processor may predict a value using eqn. 6. In step S940 the processor sets a value of the target field for the target record to the predicted value. Finally, in step S945 the processor determines if the dataset includes missing values. For example, the processor may perform a search of the dataset (e.g., for empty fields and/or fields with a value equal to NaN). If the dataset includes missing values processing returns to step S905. Otherwise, processing ends.

Listing 1 is pseudo code of an example implementation of the steps described with regard to FIG. 9. Lines 1-26 describe the main flow, where pre-processing is implemented in lines 11-14, bi-local linear model construction and parameter estimation is implemented in lines 15-24, and the missing value is lastly imputed. In the following parts, lines 27-42 describe a mean imputation method for data pre-processing, and lines 43-50 illustrates an example algorithm to find k nearest neighbor records to the selected target record, and lines 51-61 describe an estimation method for center and width parameters in radial basis functions.

```
Imputation
1.   % D: PHR dataset
2.   % y_ij: missing data of i-th record and j-th feature
3.   % NaN: not a number
4.   % X: input matrix of the training data
5.   % B: output vector of the training data
6.   % θ_p: parameters for radial basis function
7.   % NumOfFea: number of features in training data
8.   FUNCTION Imputation
9.   BEGIN
10.     WHILE missing data existed
11.       Recover the remaining missing data as NaN
12.       FIND the feature j with minimal missing values
13.       SELECT a missing data to be imputed as y_ij
14.       CALL Function Mean_Imputation (D, k)
15.       CALL X=Function KNN(D(i,:),k)
16.       K1 = SELECT quantitative features FROM X
17.       K2 = SELECT qualitative features FROM X
18.       θ_1 = CALL Function RBF_Para(K1)
19.       θ_2 = CALL Function RBF_Para(K2)
20.       FOR i = 1 : NumOfFea
21.         CalculateR_1(X_i, θ_1) and R_2(X_i, θ_2)
22.         CalculatedΦ(X_i) = [X_iR_1(X_i), X_iR_2(X_i)]
23.       END
24.       Θ = inv(Φ)B
25.       Y_ij = Φ(C)^T Θ
26.   END
% Mean_Imputation
27.  % NumOfRec: number of records in PHR data
28.  % NumOfFea: number of features in PHR data
29.  % NaN: not a number
30.  % D: PHR database
31.  % IndOfNonMis: index of non-missing data
32.  % NumOfNonMis: number of non-missing data
33.  FUNCTION Mean_Imputation(D)
34.  BEGIN
35.  FOR p = 1 : NumOfFea
```

```
36.     [IndOfNonMis, NumOfNonMis ] = Find(D(:,p)! = NaN)
37.     FOR q = 1 : NumOfRec
38.        IF D(p,q) == NaN
39.           D(p,q) = SUM(D(:,IndOfNonMis))/NumOfNonMis
40.        END
41.     END
42. END
% KNN
43. FUNCTION X=KNN(D(i,:), k)
44. BEGIN
45.     FOR p = 1 : i-1, i+1 : NumOfRec
46.        Dis(p)=Distance(D(i,:) and D(p,:))
47.     END
48.     Ind = SORT (Dis(p))
49.     X = D(Ind(1:k), :)
50. END
% RBF_Para
51. % k: number of nearest neighbor
52. % K: quantitative or qualitative data
53. % NumOfFea: number of quantitative features or qualitative features
54. FUNCTION θ= RBF_Para(K)
55. BEGIN
56.     FOR i = 1 : NumOfFea
57.        Mu(i) = sum(K(1:k,i))/k
58.        Sigma = var(K(1:k,:))
59.     END
60.     θ = [Mu, Sigma]
61. END
```

Some of the above example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed above, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a storage medium. A processor(s) may perform the necessary tasks.

Specific structural and functional details disclosed herein are merely representative for purposes of describing example embodiments. Example embodiments, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

It should also be noted that in some alternative implementations, the functions/acts noted may occur out of the order noted in the figures. For example, two figures shown in succession may in fact be executed concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the above example embodiments and corresponding detailed description are presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the above illustrative embodiments, reference to acts and symbolic representations of operations (e.g., in the form of flowcharts) that may be implemented as program modules or functional processes include routines, programs, objects, components, data structures, etc., that perform particular tasks or implement particular abstract data types and may be described and/or implemented using existing hardware at existing structural elements. Such existing hardware may include one or more Central Processing Units (CPUs), digital signal processors (DSPs), application-specific-integrated-circuits, field programmable gate arrays (FPGAs) computers or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

Note also that the software implemented aspects of the example embodiments are typically encoded on some form of non-transitory program storage medium or implemented over some type of transmission medium. The program storage medium may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

Lastly, it should also be noted that whilst the accompanying claims set out particular combinations of features described herein, the scope of the present disclosure is not limited to the particular combinations hereafter claimed, but instead extends to encompass any combination of features or embodiments herein disclosed irrespective of whether or not that particular combination has been specifically enumerated in the accompanying claims at this time.

What is claimed is:

1. A method, comprising:
   in a dataset including a plurality of records, at least one of the plurality of records including one or more field having a missing value, wherein completing the dataset includes:
      selecting a target record from the dataset, the target record being one of the plurality of records including a missing value;
      partitioning a portion of the plurality of records of the dataset into at least two groups of columns including co-related data, the portion of the plurality of records being selected from the plurality of records and including records having a value for a same field as the missing value in the target record;
      predicting the missing value based on a relationship between fields in each of the at least two groups of columns associated with the partitioned records; and
      setting the field including the missing value of the target record to the predicted value;
   wherein predicting the missing value includes:
      generating a first linear function based on a first type of co-related data;
      generating a second linear function based on a second type of co-related data;
      generate a bi-local linear local model based on the first linear function and the second linear function; and
      predicting the missing value using the bi-local linear local model.

2. The method of claim 1, wherein selecting the target record from the dataset includes selecting the target record as a record with a fewest number of missing values.

3. The method of claim 1, further comprising:
   selecting a target field from the target record, the target field including the missing value.

4. The method of claim 1, wherein partitioning the records of the dataset into at least two groups includes:
   filtering the dataset to exclude from the dataset those records missing values for at least one target field, the at least one target field including the missing value.

5. The method of claim 1, wherein partitioning the records of the dataset into at least two groups includes:
   determining a mean or average value for a target field, and inserting the mean or average value as a temporary value for each record missing a corresponding value for the target field.

6. The method of claim 1, wherein partitioning the records of the dataset into at least two groups includes:
   selecting k-nearest neighbor (KNN) records of the target record.

7. The method of claim 1, wherein
   the first type of co-related data is based on quantitative data; and
   the second type of co-related data is based on qualitative data.

8. The method of claim 1, wherein the dataset is selected from a personal health record (PHR) database.

9. A non-transitory computer-readable storage medium having stored thereon computer executable program code which, when executed on a computer system, causes the computer system to perform steps comprising:
   in a dataset including a plurality of records, at least one of the plurality of records including one or more field having a missing value, wherein completing the dataset includes:
      select a target record from the dataset, the target record being one of the plurality of records including a missing value;
      partition a portion of the plurality of records of the dataset into at least two groups of columns including co-related data, the portion of the plurality of records being selected from the plurality of records and including records having a value for a same field as the missing value in the target record;
      predict the missing value based on a relationship between fields in each of the at least two groups of columns associated with the partitioned records; and
      set the field including the missing value of the target record to the predicted value;
   wherein predicting the missing value includes:
      generating a first linear function based on a first type of co-related data;
      generating a second linear function based on a second type of co-related data;
      generate a bi-local linear local model based on the first linear function and the second linear function; and
      predicting the missing value using the bi-local linear local model.

10. The non-transitory computer-readable storage medium of claim 9, wherein selecting the target record from the dataset includes selecting the target record as a record with a fewest number of missing values.

11. The non-transitory computer-readable storage medium of claim 9, wherein the step further comprising:
   select a target field from the target record, the target field including the missing value.

12. The non-transitory computer-readable storage medium of claim 9, wherein partitioning the records of the dataset into at least two groups includes:
   filtering the dataset to exclude from the dataset those records missing values for at least one target field, the at least one target field including the missing value.

13. The non-transitory computer-readable storage medium of claim 9, wherein partitioning the records of the dataset into at least two groups includes:

determining a mean or average value for a target field, and
inserting the mean or average value as a temporary value for each record missing a corresponding value for the target field.

14. The non-transitory computer-readable storage medium of claim 9, wherein partitioning the records of the dataset into at least two groups includes:
selecting k-nearest neighbor (KNN) records of the target record.

15. The non-transitory computer-readable storage medium of claim 9, wherein
the first type of co-related data is based on quantitative data; and
the second type of co-related data is based on qualitative data.

16. The non-transitory computer-readable storage medium of claim 9, wherein the dataset is selected from a personal health record (PHR) database.

17. An apparatus including a processor and a non-transitory computer readable medium, the apparatus comprising:
a value prediction module configured to complete a dataset, the dataset including a plurality of records, at least one of the plurality of records including one or more field having a missing value, wherein the completing of the dataset includes:
  select a target record from the dataset, the target record being one of the plurality of records including a missing value; and
  set the field including the missing value of the target record to a predicted value; and
a model generation module configured to:
  partition a portion of the plurality of records of the dataset into at least two groups of columns including co-related data, the portion of the plurality of records being selected from the plurality of records and including records having a value for a same field as the missing value in the target record; and
  predict the missing value based on a relationship between fields in each of the at least two groups of columns associated with the partitioned records;
wherein predicting the missing value includes:
  generating a first linear function based on a first type of co-related data;
  generating a second linear function based on a second type of co-related data;
  generate a bi-local linear local model based on the first linear function and the second linear function; and
  predicting the missing value using the bi-local linear local model.

* * * * *